United States Patent
Lazzara

(10) Patent No.: US 6,287,116 B2
(45) Date of Patent: *Sep. 11, 2001

(54) DENTAL IMPLANT SYSTEM HAVING IMPROVED STABILITY

(75) Inventor: Richard J. Lazzara, Lake Worth, FL (US)

(73) Assignee: Implant Innovations, Inc., Palm Beach Gardens, FL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/241,551

(22) Filed: Feb. 1, 1999

Related U.S. Application Data

(63) Continuation of application No. 09/061,689, filed on Apr. 16, 1998, now Pat. No. 5,879,161
(60) Provisional application No. 60/059,307, filed on Sep. 17, 1997, and provisional application No. 60/043,106, filed on Apr. 17, 1997.

(51) Int. Cl.[7] ................................................. A61C 8/00
(52) U.S. Cl. .................... 433/173; 433/172; 433/201.1
(58) Field of Search .......................... 433/172, 173 OR, 433/174, 175, 176, 201.1

(56) References Cited

U.S. PATENT DOCUMENTS

| | | | |
|---|---|---|---|
| 4,713,003 | * 12/1987 | Symington et al. | 433/173 |
| 5,244,390 | 9/1993 | Lazzara et al. | 433/143 |
| 5,429,505 | 7/1995 | Fortin | 433/173 |
| 5,478,237 | 12/1995 | Ishizawa | 433/201.1 |
| 5,482,463 | 1/1996 | Wilson, Jr. et al. | 433/173 |
| 5,573,401 | 11/1996 | Davidson et al. | 433/173 |
| 5,711,669 | * 1/1998 | Hurson | 433/174 |
| 5,833,463 | 11/1998 | Hurson | 433/173 |
| 5,885,078 | * 3/1999 | Cagna et al. | 433/172 |

OTHER PUBLICATIONS

Antler, M., *Structure Of Polymer Codeposited In Gold Electroplates*, Plating, pp. 468–473 (1973).
Gaensheimer, Josef, *The Lubrication Of Threads With Solid Lubricants*, Proceedings of the Japan International Tribology Conference in Nagoya, pp. 1107–1110 (1990).
Garte, Samuel, M., *Effect Of Substrate Roughness On The Porosity Of Gold Electrodeposits*, Plating, pp. 1335–1339 (Nov. 1996).
Laepple, Werner et al., *New Surface Treatment For Screw Threads*, Journal of the American Society of Lubrication Engineers, pp. 227–231 (Apr. 1983).
Sato, Takehiko et al., *Palladium With A Thin Gold Layer As A Sliding Contact Material*, IEEE Transactions On Components, Hybrids, And Manufacturing Technology, vol. CHMT–4, No. 1, pp. 10–14 (Mar. 1981).
Spalvins, Talivaldis et al., *Frictional And Morphological Characteristics Of Ion–Plated Soft Metallic Films*, Thin Solid Films, vol. 84, pp. 267–272 (1981).
Willis, David P., Jr., *Fighting Friction With Bonded Coatings*, Machine Design, pp. 123–128 (Apr. 10, 1980).
Brochure entitled "Gold Screws" by Implant Innovations, Inc. (1987).
Computer–assisted search for "Screws–Plating Friction Reducing," Nerac Inc., pp. 1–10 (Feb. 26, 1997).
Computer–assisted search for "Screws–Plating Friction Reducing Patents," Nerac Inc., pp. 1–18 (Feb. 26, 1997).
Computer–assisted search for "Screws–Friction Reducing Patents and Articles Gold Plating," Nerac Inc., pp. 1–9 (Feb. 28, 1997).

* cited by examiner

*Primary Examiner*—John J. Wilson
(74) *Attorney, Agent, or Firm*—Jenkens & Gilchrist

(57) ABSTRACT

Improved tensioning or preloading of screws used to assemble dental implants is made possible by using screws which have a coating of gold, particularly screws made of palladium alloy or of titanium or a titanium alloy which has been plated with a different biocompatible metal, such as platinum, nickel or copper. The increased preload improves the stability of the dental implant assembly because greater mastication forces are then required to pry apart contiguous components of the implant assembly and bend the screws.

9 Claims, 8 Drawing Sheets

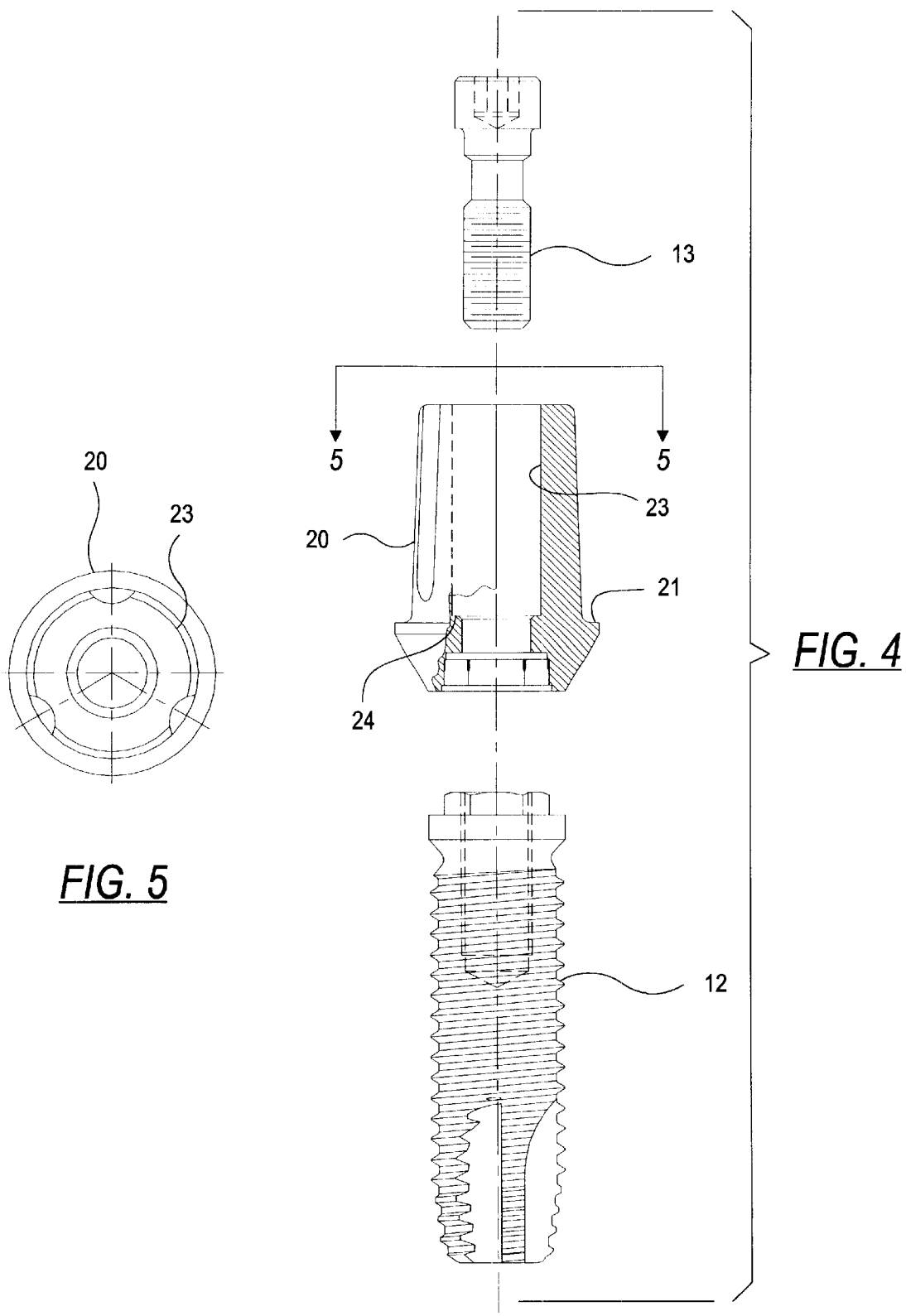

DENTAL IMPLANT SYSTEM HAVING IMPROVED STABILITY

RELATED APPLICATION

This application is a continuation of U.S. application Ser. No. 09/061,689, filed Apr. 16, 1998, now U.S. Pat. No. 5,879,161, which claim the benefit of application of U.S. application Ser. No. 60/043,106, filed Apr. 17, 1997, and U.S. application Ser. No. 60/059,307, filed Sep. 17, 1997.

BACKGROUND OF THE INVENTION

This invention relates to the field of dental implants, more particularly, to the components used in dental implant systems and, most particularly, to the screws which are used to assemble such systems.

Dental implants are the subject of many patents and extensive literature. Artificial roots are implanted in the jawbones of patients and used to support replacement teeth. The tooth may be fastened directly to the root or it may be fastened to an intermediate part, called an abutment. In most systems, small screws are used to connect the parts. The screws which are used to connect the abutment to the implanted root typically have minor diameters of about 0.055–0.059 inch (1.4–1.5 mm). Retaining screws, which hold the tooth to the abutment part, may have minor diameters of about 0.0419–0.0453 inch (1.06–1.15 mm). Such screws are made of various metals and alloys, particularly, palladium, titanium and gold alloys, which are biocompatible and have become accepted for dental use.

It will be apparent that when such implanted artificial teeth are used to chew food (mastication), they are subject to significant forces. These forces place loads on the screws holding the tooth and any abutment to the implanted root. While those screws are intended to prevent the components of the implant system from separating, the mastication loads may cause the contacting surfaces of the components to open slightly on one side of the implant system by bending one or more of the screws. This creates what will be referred to herein as a "microgap," which typically occurs at the interface between the opposed surfaces of the abutment and the implanted root. Oral fluids may gain access to the interior of the implant system through the microgap, risking infection. Movement of the implant components may also cause the screws to loosen or fail as they are repeatedly stretched and bent. Avoiding the forces on the implant system is not within the control of the implant designer or the dentist who installs the implant. What they can do, however, is pretension the screws to attempt to prevent the forces encountered during use from causing separation of the individual components of the implant system.

As a screw is fully threaded into a prethreaded bore, the screw is tensioned between the engaging threaded surfaces of the screw and the bore, and the abutting surfaces of the screw head and the stationary seating surface around the bore. After the screw head seats on a stationary surface, the tension on the screw increases as the screw is threaded farther into the bore. This tension on the screw produces a force that is commonly referred to as the "preload" of the screw.

Classical screw theory relates the degree (angle) of turn of a screw to preload or clamping force by the following simplified equation:

$$F = (P\theta/360)K$$

where:

F=preload or clamped force of the two parts held together by the screw (e.g., the abutment to the implant), P=pitch of the abutment screw (e.g., 0.4 mm for a typical abutment screw), $\theta$=degree (angle) of turn measured after snugging of screw head against opposed surface (i.e., abutment/implant surfaces are seated together), and K=spring constant of the screw and joint.

If the degree of turn ($\theta$) is increased, the resulting clamping force (F) is also increased. An increase in the clamping force results in a tighter abutment/implant joint. The tighter joint imparts greater resistance to screw loosening and increases the load required to pry the abutment/implant joint apart. Side loads produced during mastication result in forces that tend to pry the abutment/implant joint apart. Joint prying and fatigue strength are directly related and, thus, the greater the force required to pry the joint, the greater the force required to cause cyclic fatigue failure of the screw.

In general, the fatigue strength of the screw increases as the preload increases because the screw remains more stable when subjected to various loads. The farther a screw is threaded into its bore after seating of the screw head, the greater the preload on the screw, i.e., the greater the force exerted by the inherent resilience (elastic recovery) of the screw itself on the opposing surfaces responsible for the tension on the screw. Advancing movement of the screw into its bore is resisted in part by the friction between the rotating surfaces of the screw and the opposed stationary surfaces, which must be overcome by the applied torque to advance the screw. By reducing the friction between the rotating surfaces of the screw and the opposed stationary surfaces, the preload on the screw can be increased for any applied torque because that torque will cause the screw to be advanced farther into its bore.

SUMMARY OF THE INVENTION

The primary object of the present invention is to provide an improved way to increase the preload on the screw and thereby improve the stability of the dental implant assembly and the prosthesis mounted thereon.

In accordance with the present invention, the foregoing objective is realized by providing an improved dental implant system comprising an artificial root, an abutment, and a gold-plated screw fastening the abutment to the artificial root. Preferred are a palladium alloy screw or a titanium alloy screw plated with gold over an intermediate plating of a different biocompatible metal. The gold plating on the screw has been found to permit a significant increase in the preload for any applied torque, without significantly increasing the manufacturing cost of the screw. Because of the increased preload, the stability of the implant system is significantly improved which, in turn, should increase the useful life of the implant system and resistance to fatigue failure.

BRIEF DESCRIPTION OF THE DRAWINGS

FIG. 4 is an exploded view of the assembly shown in FIG. 3.

FIG. 5 is a plan view taken along line 5—5 in FIG. 4.

DESCRIPTION OF ILLUSTRATIVE EMBODIMENTS

When an artificial tooth is employed in chewing food, the forces exerted on the tooth are not all aligned with the vertical axis on which the tooth was assembled. Forces are applied at various angles off the vertical axis, producing corresponding stresses on the screw or screws which hold the implant system together. If the applied force exceeds the strength of a screw, the screw can bend and open a microgap where the implanted root meets the abutment or the abutment meets the tooth. Repeated bending of the screw can lead to breakage. Also, fluids from the mouth may enter the microgap and lead to infection.

Figure 1:
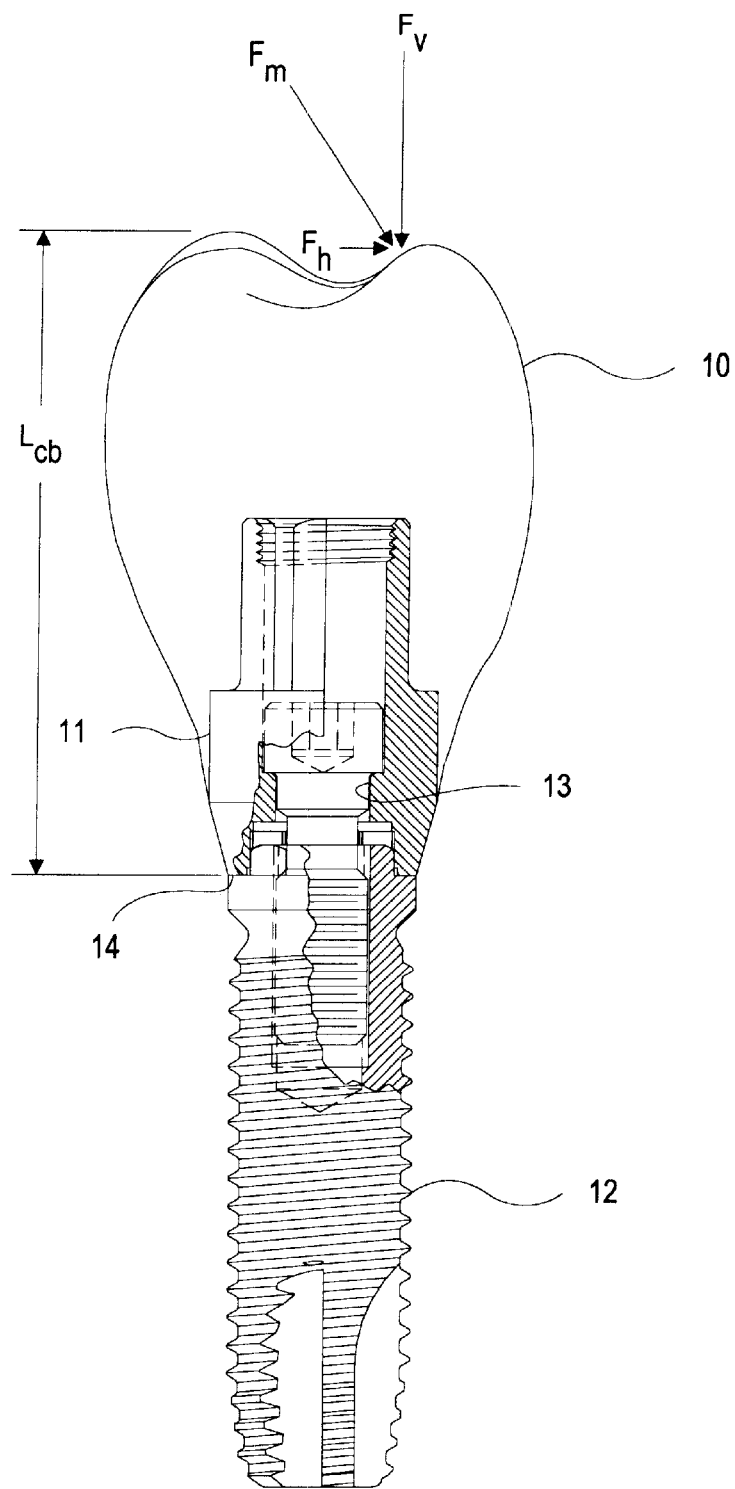
FIG. 1 is a side elevation, partially in section, of a dental implant abutment system embodying the invention.

The potential problems may be illustrated by considering the implant system shown in FIG. 1, which illustrates an artificial tooth 10 formed on an abutment 11 and secured to an implanted root 12 by means of a screw 13. The threaded portion of the screw 13 engages corresponding threads in a bore inside the implanted root 12. When the screw 13 is tightened, it is placed under tension by applying a predetermined drive torque to the screw. As described above, this produces a preload on the screw.

When the forces exerted in mastication exceed the preload on the screw, the screw will bend under stress and allow a microgap to open. In FIG. 1, such a gap could open at the junction 14 where the abutment 11 meets the top of the implanted root 12. FIG. 1 illustrates an off-axis mastication force $F_m$ exerted on the tooth, and shows that this force may be resolved into a vertical force component $F_v$ and a horizontal force component $F_h$. The bending force exerted on the screw 13 at the junction 14 may be expressed as $$(F_h)(L_{cb})$$

where $L_{cb}$ is the distance from the top of the tooth to the junction 14.

The resisting force $F_s$ exerted by the pretensioning of the screw 13 may be expressed as $$(F_s)(W/2)$$

where W is the minor diameter of the threaded portion of the root 12. If the two forces $F_h$ and $F_s$ are equal so that the screw begins to bend, then $$(F_s)(W/2)=(F_h)(L_{cb})$$

and $$F_s=(F_h)(L_{cb})/(W/2).$$

From this equation, it can be concluded that increasing the resisting force $F_s$ by greater pretensioning of the screw 13 will permit a higher mastication force $F_m$ to be exerted on the tooth before the screw 13 bends and opens a microgap.

Figure 2:
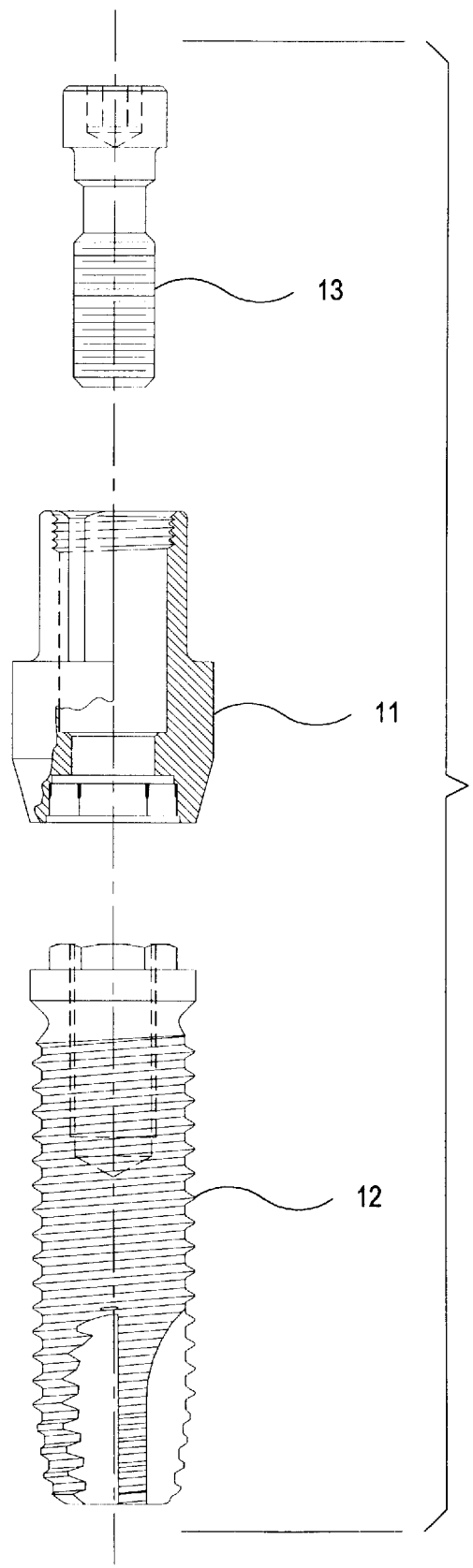
FIG. 2 is an exploded view of the assembly shown in FIG. 1.
Figure 3:
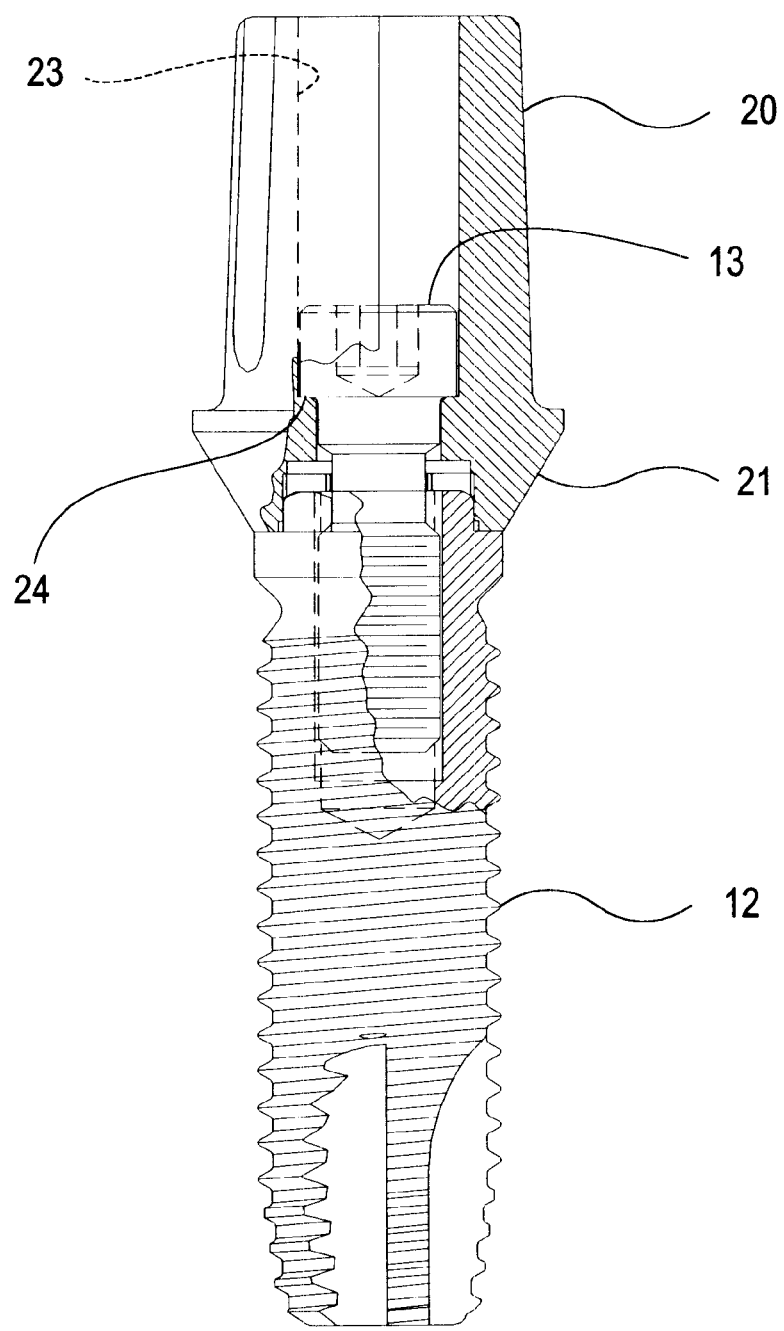
FIG. 3 is a side elevation, partially in section, of a second dental implant abutment system embodying the invention.

The particular abutment 11 illustrated in FIGS. 1 and 2 is intended for use in single-tooth applications. FIGS. 3–11 illustrate the use of the same implant or artificial root 12 and screw 13 with three different abutments 20, 30 and 40. The abutment 30 illustrated in FIGS. 3–5 is a healing abutment having a widely flared transmucosal section 21. This abutment forms a central passageway 23 and shoulder 24 for passing the screw 13 and seating the head of the screw inside the abutment.

Figure 6:
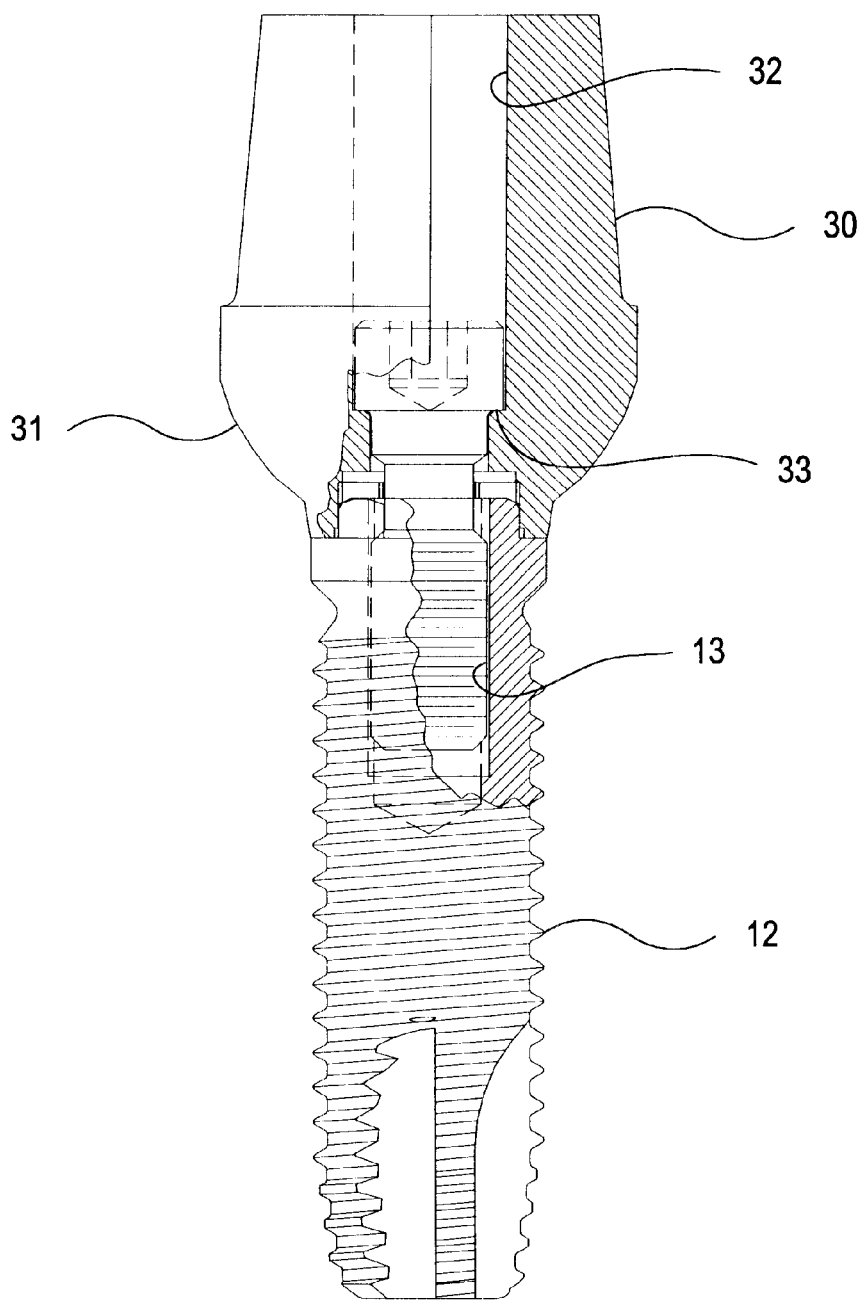
FIG. 6 is a side elevation, partially in section, of a third dental implant abutment system embodying the invention.
Figures 7, 8:
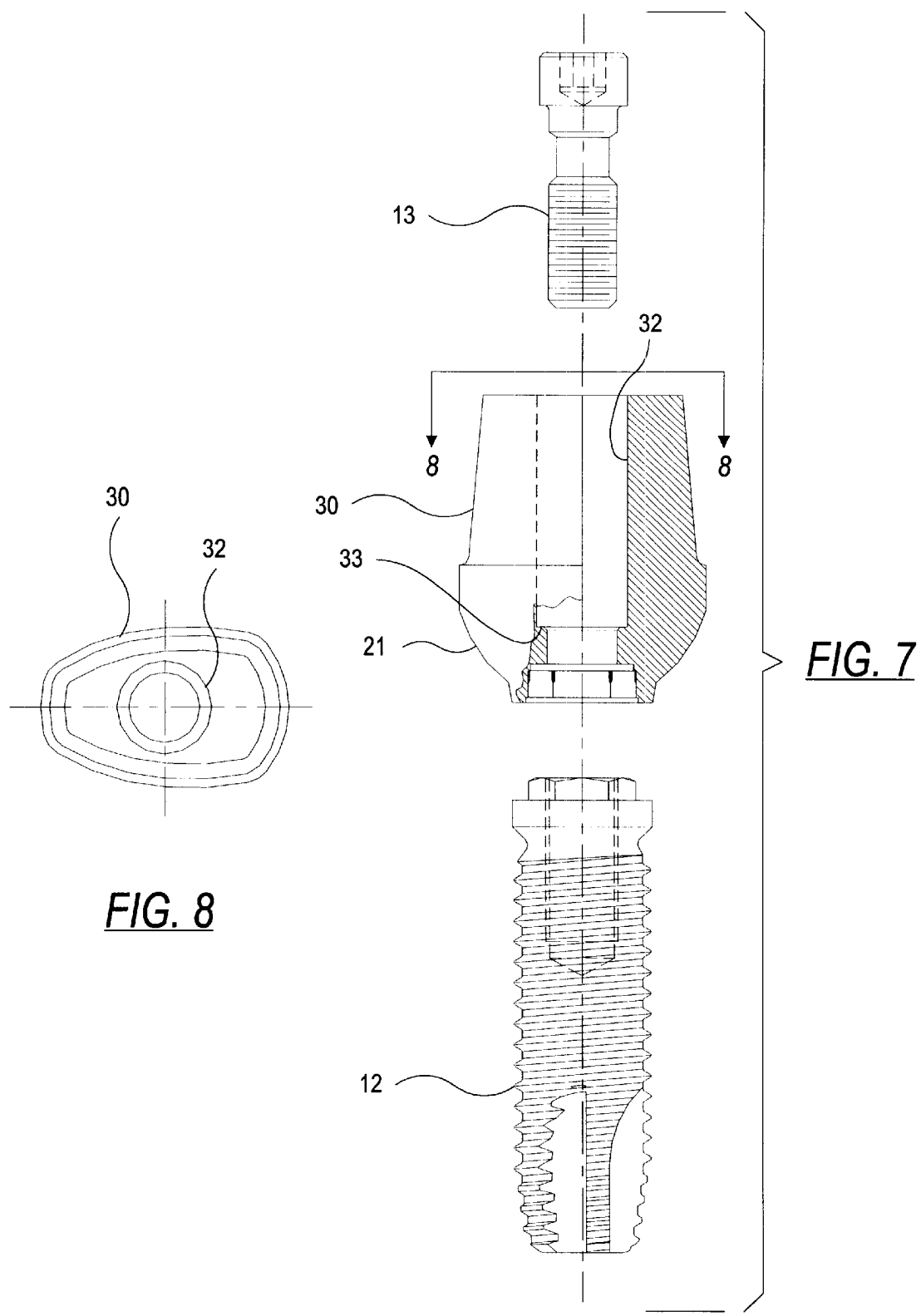
FIG. 7 is an exploded view of the assembly shown in FIG. 6.
FIG. 8 is a plan view taken along line 8—8 in FIG. 7.

The abutment 30 shown in FIGS. 6–8 is another healing abutment having a differently shaped transmucosal section 31. Again, the central portion of the abutment 30 forms a longitudinal passageway 32 for receiving the screw 13, and a shoulder 33 for seating the head of the screw 13 within the abutment. As can be seen in FIG. 8, the abutment 30 has a nonround cross-section to approximate the shape of the tooth being restored.

Figure 9:
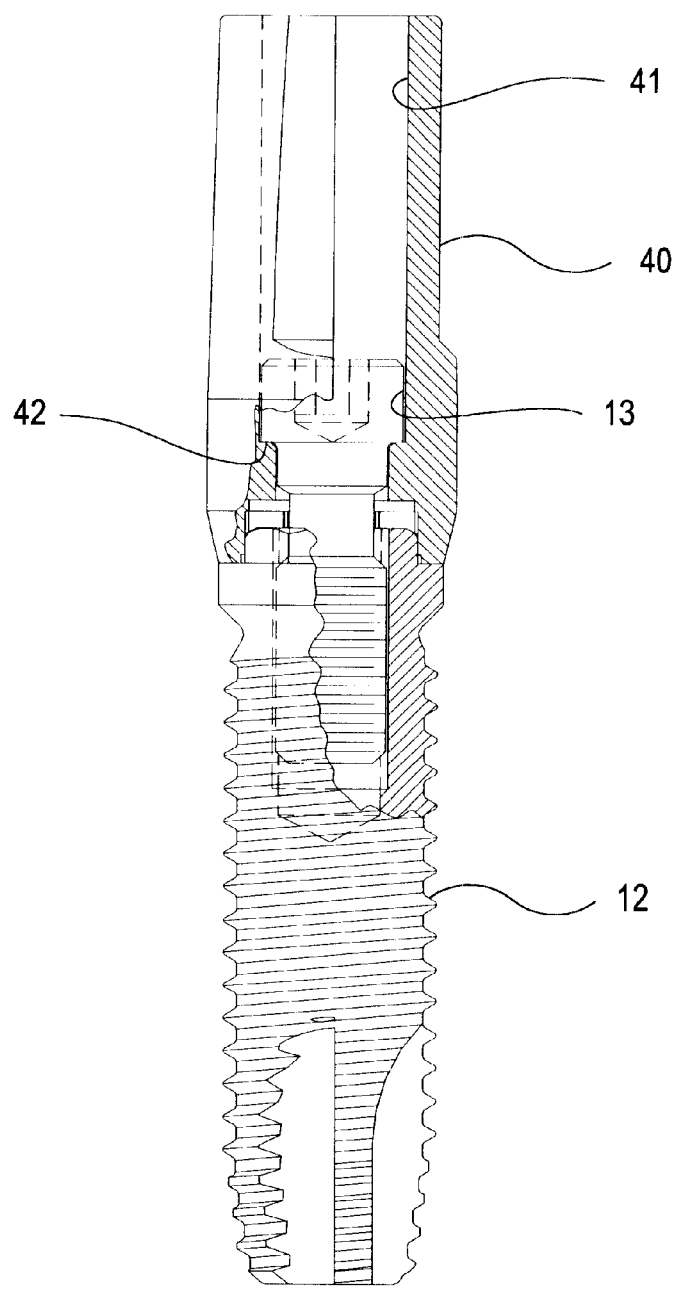
FIG. 9 is a side elevation, partially in section, of a fourth dental implant abutment system embodying the invention.
Figures 10, 11:
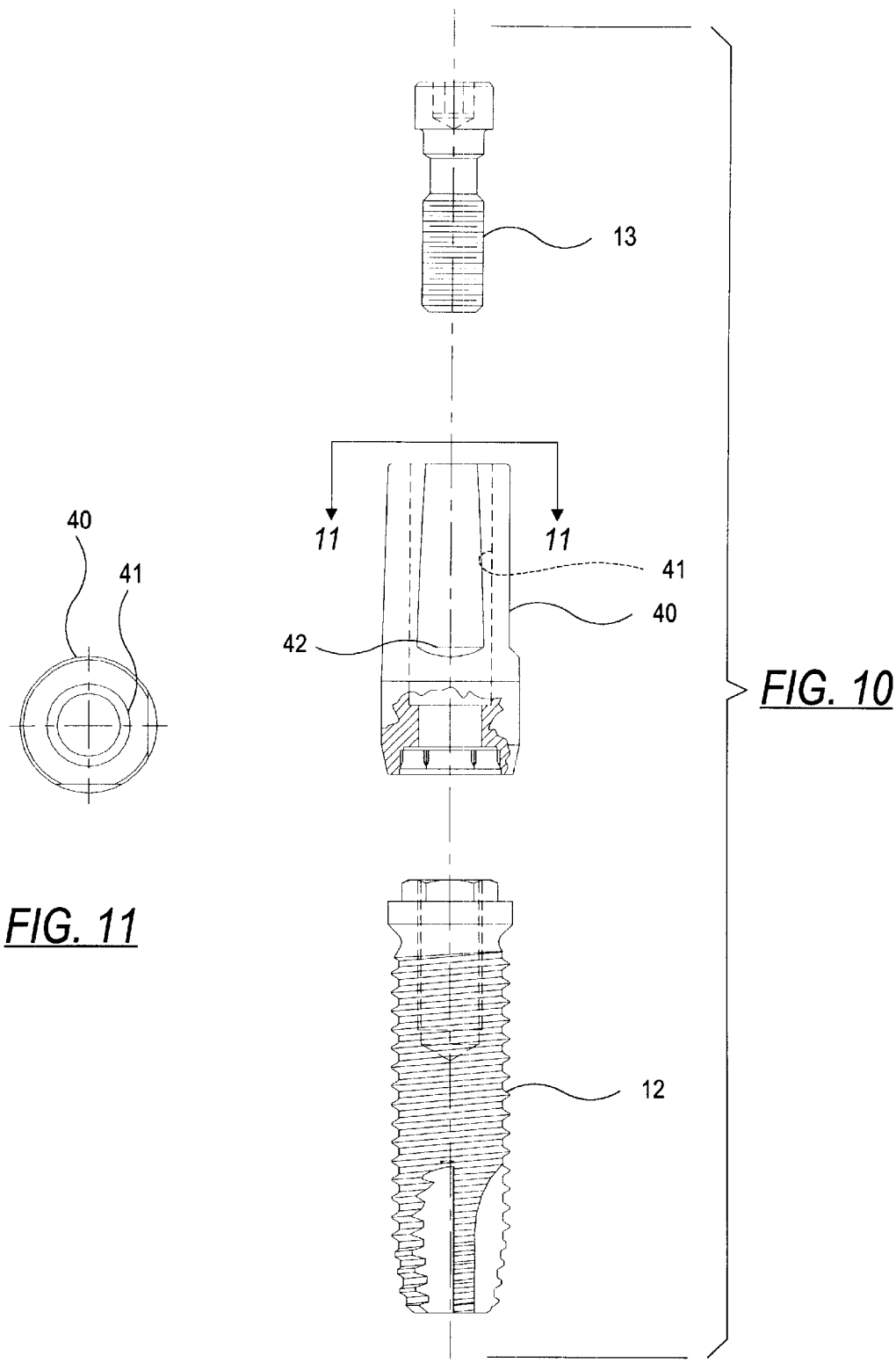
FIG. 10 is an exploded view of the assembly shown in FIG. 9.
FIG. 11 is a plan view taken along line 11—11 in FIG. 10.

FIGS. 9–11 illustrate a standard abutment known in the industry as the "UCLA" abutment 40, which forms an internal passageway 41 for passing the screw 13, and a shoulder 42 for seating the head of the screw 13 inside the abutment.

Screws used to assemble dental implant systems are typically tightened with a predetermined torque which is great enough to produce a substantial preload on the screw, but not so great as to risk fracturing the metal. This applied torque must overcome the frictional forces associated with the thread engagement and with turning the screw head against its seating surface, and must also tension the body of the screw.

As discussed above, the screws used in assembling dental implants are very small, and the loads which can applied to them are limited. While they are generally sufficient for dental implants to provide satisfactory service, it would be desirable to be able to apply even greater torque so as to minimize the possibility of opening microgaps during mastication. Stronger screws would be desirable, but the strength of screws is determined primarily by the metal used, and not all metals are biocompatible and acceptable for dental use. In general, if a metal or alloy is biocompatible and has sufficient strength, it may be used to make screws for dental implant systems. A commonly used metal is titanium or alloys, such as Ti $Al_6$ $V_4$ (titanium containing 6% aluminum and 4% vanadium) and Ti 1313 (titanium containing 13% zirconium and 13% niobium). Such screws may be coated with malleable metals or polymers to increase preloading as disclosed in U.S. Pat. No. 5,711,669. The inventor has found that palladium alloy screws have advantages over titanium alloys. Palladium alloys having sufficient strength, such as palladium alloy 8010 (palladium containing 9.5–10.5% gallium, 6.5–7.5% copper, and 1.8–2.2% gold with traces of zinc, iridium, and ruthenium), are particularly useful. Some palladium alloys, e.g., alloy 8010, are stronger than titanium and its alloys. Thus, they are inherently better able to accept increased preloading compared to titanium. Additionally, using palladium alloy screws with titanium implants may reduce the resistance to tightening experienced with titanium screws. Their performance is further enhanced by coating with gold. Platinum alloys containing iridium may also have application as dental implant screws.

Both the artificial roots and the abutments used in dental implant systems are typically made of titanium or a titanium alloy. The present invention reduces the problems associated with the screws presently used in such systems and makes it possible to apply higher preloads to the screws. The result is an improved implant assembly which is more stable, e.g., more resistant to the opening of microgaps and the associated problems and has increased resistance to fatigue failure.

The screws used in this invention are necessarily the same size as the screws which they replace. With the gold plating, however, a greater portion of the torque applied to the screw during assembly is applied to pretensioning the body of the screw and less to overcoming frictional forces. This increased pretensioning increases the force required to open a microgap in a dental implant system using the gold-plated screw, reduces the size of the microgap opened by forces between the threshold level at which a gap is initially opened and the fracture level, and increases the fatigue strength of the screw. This improvement is made possible by coating the screws, preferably by electroplating, with a thin layer of gold. The gold coating is believed to act as a lubricant or anti-gauling agent so that the torque which is applied places a greater tensile stress on the screw body. In addition, the gold provides improved corrosion resistance.

The screw threads may be machined or the metal stock may be roll threaded. After being threaded, the screws are coated with substantially pure gold. The thickness of the gold is limited by the space between the threads and, consequently, should be quite thin, typically 0.5–1 $\mu$m. Since the metal threads will have an inherent surface roughness, the gold plating should be sufficient to significantly reduce the frictional forces resulting from the surface roughness.

The gold plating may be applied to screws made of any of the standard alloys described above. Plating of gold directly onto palladium alloys is satisfactory. When the screw is made of titanium or a titanium alloy, the screw should be plated with an intermediate material such as platinum, nickel or copper before it is plated with gold to achieve good bonding of the gold to the titanium or titanium alloy. When gold is plated directly onto titanium or a titanium alloy, adhesion is relatively poor. The fragments of the gold plating can become detached from the substrate during use of the screw. An intermediate "strike" of a biocompatible material such as platinum, nickel or copper causes the gold plating to become more permanently bonded to the titanium or titanium alloy. The same technique may be used with other metals, such as palladium alloys, if desired.

EXAMPLE 1

An experiment was conducted to simulate the reaction of a dental implant abutment assembly to forces imposed on it. In this experiment, screws machined from an 8010 palladium alloy were used to fasten an abutment to a dental implant. Some of the screws were used as made ("8010"), while others were plated with gold to a thickness of 0.5–1 $\mu$m ("8010PL"). The screws were driven until initial contact was made by the screw head with the seating surface. Then the screws were tightened with applied torques of 45, 38 and 32 Newton-centimeters (N-cm) to preload the screws. Using a 360° template placed around the implant, the angle through which each screw was turned by the applied torque, after initial contact with the seating surface, was measured and recorded. The off-axis forces (in Newtons) required to open microgaps of 0.25 mils were also recorded.

A compressive force was applied to the abutment at an angle of 30° from the central axis of the abutment and the implant to simulate an off-axis force imposed on the screw during mastication, as discussed above. The compressive force was applied by placing the implant/abutment assembly in a standard tensile/compression test apparatus at a 30° angle to the vertical axis. An optical micro camera was aimed at the junction between the abutment and the implant so that the width of any microgap at that junction could be measured, at a 350× magnification. The applied force was gradually increased until a 0.25-mil microgap was opened. The magnitude of the applied force was recorded when the microgap reached 0.25 mil.

The fatigue strength of the screws was measured in a similar manner. A titanium implant was anchored in simulated bone material, and a titanium alloy (Ti Al$_6$ V$_4$) abutment simulating a large molar 17 mm high was mounted on the implant with an abutment screw. The resulting assembly simulates a single tooth replacement. It is fixed to the base of a compression testing apparatus at a 30° angle from the vertical. A stainless steel probe contacts the top of the abutment and places a vertical load to simulate the forces of mastication experienced by a tooth. A predetermined load is applied which cycles between 10–100% of the maximum load. The data presented below gives the maximum load which could be applied for five million cycles without failure.

The results are shown in Table A.

TABLE A

Angle of Turn, Gap and Fatigue at Various Drive Torques

| | No Plating 80/10 UCLA | | | Gold-Plated 80/10 UCLA | | |
|---|---|---|---|---|---|---|
| Drive Torque | Turn Angle | 30+ C. Gap Pry Load | Fatigue Strength | Turn Angle | 30+ C. Gap Pry Load | Fatigue Strength |
| 32 N cm | 19° C. | 240 N | 275 N* | 28° C. | 345 N | 325 N* |
| 38 N cm | 23° C. | 290 N | | 36° C. | 390 N | |
| 45 N cm | 25° C. | 310 N | | 40° C. | 411 N | |

*No failure after 5 million cycles.

As can be seen from the above data, any given torque turned the plated screws through a greater angle than the unplated screws. The greater angular displacement produced a greater preload or tension in the plated screws, as evidenced by the fact that a greater off-axis force was required to open the microgap. This means that the gold-plated screws will resist greater masticating loads than the conventional unplated screws. Compare, for example, the data for the two screws which were tightened with a torque of 45 N-cm. The difference in the loads which the screws could accept before a 0.25 mil microgap was opened was 101 N, or an improvement of more than 30%. Thus, the plated screw permits the attainment of a more stable implant system. The greater the tension in the abutment screw, the greater the resistance to gapping. Restricted gapping is directly related to increased fatigue strength and reduced screw loosening. Fatigue failure and screw loosening are a function of cyclical loading experienced during mastication.

What is claimed is:

1. A dental implant system comprising an artificial root of titanium or titanium alloy and an abutment of titanium or titanium alloy fastened together by a screw having a body made of gold alloy, and a coating of gold on said body, thereby making possible an increased tensioning of said screw compared to the same screw without said coating.

2. The dental implant system of claim 1, wherein said coating is substantially pure gold.

3. The dental implant system of claim 1, wherein said coating is electroplated on said body.

4. The dental implant system of claim 1, wherein said coating has a thickness in the range of from about 0.5 to about 1 $\mu$m.

5. A method of increasing the preloading of a screw used to assemble components of a dental implant system, said method comprising:

(a) placing a first component of titanium or titanium alloy having an internal passageway in contact with a second component of titanium or titanium alloy having an internally threaded portion;

(b) passing a screw through the internal passageway of said first component and engaging the internally threaded portion of said second component, said screw having a body made of gold alloy, and a coating of gold on said body, thereby making possible an increased tensioning of said screw compared to the same screw without said coating; and (c) tightening said screw to preload said screw.

6. The method of claim 5, wherein said screw is tightened to a preselected torque.

7. The method of claim 5, wherein said coating is substantially pure gold.

8. The method of claim 5, wherein said coating is electroplated on said body.

9. The method of claim 5, wherein said coating has a thickness in the range of from about 0.5 to about 1 82 m.

* * * * *